(12) United States Patent
Scialdone et al.

(10) Patent No.: US 6,815,426 B2
(45) Date of Patent: Nov. 9, 2004

(54) ANGIOGENESIS-INHIBITORY TRIPEPTIDES, COMPOSITIONS AND THEIR METHODS OF USE

(75) Inventors: Mark A. Scialdone, Landenberg, PA (US); Shaker Ahmed Mousa, Lincoln University, PA (US); Steven W. Shuey, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/074,389

(22) Filed: Feb. 12, 2002

(65) Prior Publication Data

US 2003/0027769 A1 Feb. 6, 2003

Related U.S. Application Data

(60) Provisional application No. 60/269,537, filed on Feb. 16, 2001.

(51) Int. Cl.[7] .................. A61K 38/06; C07K 5/08
(52) U.S. Cl. ................. 514/18; 514/2; 514/209; 530/300
(58) Field of Search ................. 350/331, 300; 514/2, 18, 209

(56) References Cited

U.S. PATENT DOCUMENTS

| | | | |
|---|---|---|---|
| 5,092,885 A | | 3/1992 | Yamada et al. ............ 623/11 |
| 5,112,946 A | | 5/1992 | Maione ................... 530/324 |
| 5,187,156 A | * | 2/1993 | Matsuo et al. ............ 514/18 |
| 5,192,744 A | | 3/1993 | Bouck et al. .............. 514/8 |
| 5,202,352 A | | 4/1993 | Okada et al. ............ 574/475 |
| 6,031,072 A | * | 2/2000 | Blaschuk et al. |
| 6,169,071 B1 | * | 1/2001 | Blaschuk et al. ........... 514/4 |

OTHER PUBLICATIONS

Malle, Ernst et al. Identification of glycoprotein IIB as the lipoprotein(a)–binding protein on platelets. Arteriosclerosis and Thrombosis, vol. 14, No. 3, Mar. 1994, pp. 345–351.*

Maeshima, Yohei, Pablo Colorado, Adrianna Torre, Kathryn Holthaus, James Grunkemeyer, Mark Ericksen, Helmut Hopfer, Yingwen Xiao, Isaac Stillman and Raghu Kalluri, J. Biol. Chem., vol. 275, Issue 28, Jul. 14, 2000, pp. 21340–21348.*

Buckley, Christopher, Darrell Pilling, Nick Henriquez, Greg Parsonage, Katy Threlfall, Dagmar Scheel–Toellner, David Simmons, Arne Akbar, Janet Lord and Mike Salmon. Nature, V. 397, Feb. 11, 1999, pp. 534–539.*

Wickham, Thomas et al. Increased in vitro and in vivo gene transfer by adenovirus vectors containing chimeric fiber proteins. Journal of Virology, vol. 71, No. 11, Nov. 1999, pp. 8221–8229.*

Brown et al. Annals of Surgical Oncology, V7, N10 (Dec. 2000): p743–749.*

Mousa, S. A., Angiogenesis Inhibitors and Stimulators: Potential Therapeutic Implications, Landes Bioscience, Georgetown, TX; Chapter 1, (2000).

Breier et al., Trends in Cell Biology, 6:454–456 (1996).

Folkman, Nature Medicine 1:27–31 (1995).

Risau, Nature 386:671–674 (1997).

Blood et al., Bioch. Biophys. Acta. 1032:89–118 (1990).

Folkman et al., Science 235: 442–447 (1987).

Moses et al., Science 248: 1408–1410 (1990).

Folkman et al., Cancer Biology 3: 89–96 (1992).

Han et al. J. Biol. Chem., 272:20395–20401 (1997).

Shahan et al. Connective Tissue Res. 40: 221–232 (1999).

Shahan et al., Cancer Res., 59: 4584–4590 (1999).

Shahan et al., J. Biol. Chem. 275: 4796–4802 (2000).

Pasco et al., Cancer Res. 60: 467–473 (2000).

Maeshima et al., J. Biol. Chem. 275: 21340–21348 (2000).

* cited by examiner

*Primary Examiner*—Robert A. Wax

(57) ABSTRACT

This invention pertains to methods and compositions for inhibiting endothelial cell tube formation, the initial step of tumor angiogenesis. More specifically, the present invention relates to tripeptides that show inhibition of angiogenesis-mediated processes.

23 Claims, 8 Drawing Sheets

| TSU-Pr (human prostate) tumor | #1 | #2 | #3 | #4 | #5 | #6 |
|---|---|---|---|---|---|---|
| Initial tumor implant weight (mg) | 53.00 | 52.00 | 53.00 | 54.00 | 54.00 | 53.00 |
| After 7 days, control tumor weight (mg) | 69.90 | 66.10 | 62.50 | 75.00 | 92.70 | 72.90 |
| After 7 days: Initial wt = Total Increase in Control | 16.70 | 12.90 | 9.30 | 21.80 | 39.50 | 19.70 |
| Tumors with acetyl-SNS-carboxamide | | | | | | |
| 45 μg acetyl-acetyl-SNS-carboxamide | 48.00 | 44.70 | 53.50 | 56.80 | 49.70 | 58.20 |
| After 7 days: Inhibitor weight - Initial Implant weight | -5.20 | -8.50 | 0.30 | 3.60 | -3.50 | 5.00 |
| % of Total weight | -28.06 | -45.87 | 1.62 | 19.43 | -18.89 | 26.98 |
| % Inhibition of tumor wt by acetyl-SNS-carboxamide | 128.06 | 145.87 | 98.38 | 80.57 | 118.89 | 73.02 |

FIG. 3A

| TSU-Pr (human prostate) tumor | #7 | #8 | #9 | #10 | MEAN | STD | SEM |
|---|---|---|---|---|---|---|---|
| Initial tumor implant weight (mg) | 54.00 | 54.00 | 52.00 | 53.00 | 53.20 | 0.79 | 0.35 |
| After 7 days, control tumor weight (mg) | 72.50 | 67.40 | 78.00 | 67.40 | 72.44 | 8.46 | 2.99 |
| After 7 days: Initial wt = Total Increase in Control | 15.90 | 15.90 | 16.70 | 16.90 | 18.53 | 8.11 | 2.56 |
| Tumors with acetyl-SNS-carboxamide | | | | | | | |
| 45 μg acetyl-acetyl-SNS-carboxamide | 48.60 | 47.40 | 46.80 | 58.40 | 51.21 | 5.09 | 1.61 |
| After 7 days: Inhibitor weight - Initial implant weight | -4.60 | -5.80 | -6.40 | 5.20 | | | |
| % of Total weight | -24.82 | -31.30 | -34.54 | 28.06 | | | |
| % Inhibition of tumor wt by acetyl-SNS-carboxamide | 124.82 | 131.30 | 134.54 | 71.94 | 110.74 | 27.45 | 8.68 |

FIG. 3B

| SNS Tag ID | Tube Length (mm) 5 μg/mL/well | % Inhibition | SEM | Angiogenesis Index 15 μg/CAM | % Inhibition |
|---|---|---|---|---|---|
| EBM Control | 0.7206 +/- 0.03 | | | 51 +/- 9.7 | |
| Growth Factor Control | 1.7886 +/- 0.09 | | | 162.22 +/- 15.3 | |
| S_A_S | 1.4564 +/- 0.14 | 31.103 | 15.053 | | |
| S_O_S | 1.0423 +/- 0.12 | 69.879 | 18.343 | 70.66 +/- 7.4 | 82.31 +/- 6.6 |
| s_N_S | 1.5152 +/- 0.06 | 25.597 | 8.8465 | | |
| s_n_S | 1.8351 +/- 0.07 | -4.3596 | 6.688 | | |
| S_G_S | 1.3653 +/- 0.08 | 39.632 | 11.725 | | |
| S_E_S | 1.9891 +/- 0.08 | -18.776 | 11.056 | | |
| s_N_S | 1.3186 +/- 0.09 | 44.008 | 9.718 | | |
| s_n_s | 1.9624 +/- 0.15 | -16.273 | 23.402 | | |
| S_D_S | 1.9624 +/- 0.15 | 32.935 | 14.458 | | |

Continued from Fig. 4A

| SNS Tag ID | Tube Length (mm) 5 μg/mL/well | % Inhibition | SEM | Angiogenesis Index 15 μg/CAM | % Inhibition |
|---|---|---|---|---|---|
| S_n_S | 1.6803 +/- 0.06 | 10.141 | 6.3189 | | |
| S_N_s | 1.2702 +/- 0.22 | 48.54 | 34.054 | 85.55 +/- 9.1 | 68.93 +/- 8.19 |
| S_n_s | 1.3933 +/- 0.06 | 37.014 | 9.3608 | | |
| t4Hyp_N_S | 1.3244 +/- 0.08 | 43.462 | 9.173 | | |
| t4Hyp_N_t4Hyp | 1.9347 +/- 0.18 | -13.679 | 28.834 | | |
| S_N_t4Hyp | 0.6404 +/- 0.07 | 107.51 | 11.263 | 82.89 +/- 9.6 | 71.33 +/- 8.27 |
| S_N_S | 0.8999 +/- 0.09 | 83.213 | 10.167 | 77.11 +/- 11.1 | 76.52 +/- 9.4 |
| Control 8A029 | 0.9606 +/- 0.16 | 77.523 | 25.513 | | |

This data represents triplicate wells/peptide, 9 images/well 35,000 human endothelial cells/well This data represents N = 6 to 9 in FGF2-stimulated CAM model

FIG. 4B

ANGIOGENESIS-INHIBITORY TRIPEPTIDES, COMPOSITIONS AND THEIR METHODS OF USE

FIELD OF THE INVENTION

The present invention relates to methods of use and compositions for inhibiting endothelial cell tube formation, the initial step of tumor angiogenesis, and angiogenesis-dependent diseases in tissue, animals and humans. More particularly, the present invention relates to a tripeptide, its analogues, mimetics and chemical derivatives that show inhibition of angiogenesis-mediated processes such as cancer, ocular neovascularization, and inflammatory diseases. Anti-angiogenesis agents disclosed can be also used in conjunction with surgery, chemotherapy, radiotherapy, and laser therapy.

BACKGROUND OF THE INVENTION

Angiogenesis is the development of new blood vessels from preexisting blood vessels (Mousa, S. A., In *Angiogenesis Inhibitors and Stimulators: Potential Therapeutic Implications,* Landes Bioscience, Georgetown, Tex.; Chapter 1, (2000)). Physiologically, angiogenesis ensures proper development of mature organisms, prepares the womb for egg implantation and plays a key role in wound healing. On the other hand, angiogenesis supports the pathological conditions associated with a number of disease states such as cancer, inflammation and ocular diseases.

The development of vascular networks during embryogenesis or normal and pathological angiogenesis depends on growth factors and cellular interactions with the extracellular matrix (Breier et al., *Trends in Cell Biology* 6:454–456 (1996); Folkman, *Nature Medicine* 1:27–31 (1995); Risau, *Nature* 386:671–674 (1997)). Blood vessels arise during embryogenesis by two processes: vasculogenesis and angiogenesis (Blood et al., *Bioch. Biophys. Acta* 1032:89–118 (1990)). Vascular endothelial growth factor (VEGF), bFGF, IL-8 and TNF-a are some of the growth factors that play a role in pathological angiogenesis associated with solid tumors, diabetic retinopathy and rheumatoid arthritis (Folkman et al., *Science* 235:442–447 (1987)). Angiogenesis is generally absent in adult or mature tissues, although it does occur in wound healing and in embryogenesis (Moses et al., *Science* 248:1408–1410 (1990)).

Angiogenesis or "neovascularization" is a multi-step process controlled by the balance of pro- and anti-angiogenic factors. The latter stages of this process involve proliferation and the organization of endothelial cells (EC) into tube-like structures. Growth factors such as FGF2 and VEGF are thought to be key players in promoting endothelial cell growth and differentiation. The endothelial cell is the pivotal component of the angiogenic process and responds to many cytokines through its cell surface receptors and intracellular signaling mechanisms. Endothelial cells in culture are capable of forming tube-like structures that possess lumens. Therefore, endothelial cells are not only a prerequisite for neovascularization, but appear to be the basal structural requirement as well.

Angiogenesis-dependent diseases include the following: inflammatory disorders such as immune and non-immune inflammation, rheumatoid arthritis, psoriasis; ocular disorders such as diabetic retinopathy, neovascular glaucoma, retinopathy of prematurity, age-related macular degeneration, corneal graft rejection; and cancer associated disorders such as solid tumors, tumor metastases, and blood born tumors such as leukemia, angiofibroma, kaposi sarcoma, benign tumors, as well as other cancers, which require neovascularization to support tumor growth.

It has been proposed that inhibition of angiogenesis would be a useful therapy for restricting tumor growth. Inhibition of angiogenesis can be achieved by inhibiting endothelial cell response to angiogenic stimuli as suggested by Folkman et al., (*Cancer Biology* 3:89–96 (1992)), where it described examples of those endothelial cell response inhibitors such as angiostatic steroids, fungal derived products such as fumagilin, platelet factor 4, thrombospondin, alpha-interferon, vitamin D analogs and D-penicillamine. For additional proposed inhibitors of angiogenesis, see Blood et. al., *Bioch. Biophys.* Acta 1032:89–118 (1990); Moses et al., *Science* 248:1408–1410 (1990); and U.S. Pat. Nos. 5,092,885, 5,112,946, 5,192,744 and 5,202,352.

In 1997, Kefalides and co-workers at the Connective Tissue Research Institute of the University of Pennsylvania, Department of Medicine, reported that the peptide corresponding to the residue sequence 185–203 of the noncollagenous 1 (NC1) domain of the α3-chain of basement membrane collagen type IV inhibited the activation of polymorphonuclear leukocytes (PMN's) (Han et al., *J. Biol. Chem.* 272:20395–20401 (1997)). It was found that the peptide α3(IV) residues 185–203 having the sequence CNYYSNSYSFWLASLNPER (SEQ ID NO:1) promoted adhesion of human melanoma cells by 50–60% over controls and also inhibit their proliferation by 40%. Alanine substitution through the peptide sequence indicated that the observed activities were dependent on the presence of residues 189–191, referred to as the SNS sequence. The Kefalides group later reported the inhibition of melanoma cell proliferation by type IV collagen requires increased levels of cAMP (Shahan et al., *Connective Tissue Res.* 40:221–232 (1999)), the identification of CD47/integrin-associated protein (IAP) and αvβ3 as two receptors for the α3(IV) chain of type IV collagen on melanoma and prostrate cells (Shahan et al., *Cancer Res.,* 59:4584–4590 (1999)). More recently, they have reported the $Ca^{2+}$ dependency in tumor cell chemotaxis (Shahan et al., *J. Biol. Chem.* 275:4796–4802 (2000)) as well as the inhibition of expression and activation of matrix metalloproteinase by the NC1 domain of type IV collagen (Pasco et al., *Cancer Res.* 60:467–473 (2000)).

Independently, Kalluri's group from the Harvard Medical School has also reported the characterization of the two different types of anti-tumor activities (anti-proliferation and anti-angiogenic) of α3(IV) NC1 domain using both in vitro and in vivo assays (Maeshima et al., *J. Biol. Chem.* 275:21340–21348 (2000)). Collectively, these reports effectively highlight the distinct and unique anti-tumor properties of the α3(IV) NC1 domain and its potential use as a lead for small molecule, anti-tumor drug design.

Absent from these reported results is the identification of a smaller recognition epitope that retains the activities of the larger peptides. The problem to be solved, therefore, is to provide the identification of a small recognition epitope which would be the crucial step in providing a template for structure-based drug design strategies towards small molecule analogues or peptidomimetics. Such small molecules would include cyclic peptides and peptide isosteres with preferable physiochemical and pharmacokinetic properties that intervene in angiogenesis-dependent diseases such as cancer.

SUMMARY OF THE INVENTION

The invention is directed toward an angiogenesis-inhibitory tripeptide of formula aa1-aa2-aa3, having a first amino acid (aa1), a second amino acid (aa2) and a third amino acid (aa3), wherein,
(a) said first amino acid is selected from the group consisting of Ser, Thr, Ala, Phe, Tyr, Cys, Gly, Leu, Lys, Pro, Arg, Gln, Glu, Asp, Asn, His, Met, Ile, Trp, Val, diaminoproprionic acid and trans-4-hydroxyproline;
(b) said second amino acid is selected from the group consisting of Asn, Ala, Gly, Asp, Glu, Gln diaminoproprionic acid and trans-4-hydroxy-proline; and
(c) said third amino acid is selected from the group consisting of Ser, Thr, Ala, Phe, Tyr, Cys, Gly, Leu, Lys, Pro, Arg, Gln, Glu, Asp, Asn, his, met, Ile, Trp, Val, diaminoproprionic acid and trans-4-hydroxyproline.

Methods of inhibiting angiogenesis by administering the tripeptide are also provided.

BRIEF DESCRIPTION OF THE DRAWINGS

The following drawings are illustrative of embodiments of the invention and are not meant to limit the scope of the invention as encompassed by the claims.

FIG. 3 illustrates the percent inhibition of TSU-Pr (human prostate) tumor growth in the presence of SNS.

FIG. 4 illustrates the anti-angiogenic effect of SNS tripeptide analogues in human endothelial tube formation and the CAM model.

DETAILED DESCRIPTION OF THE INVENTION

Figure 1A:
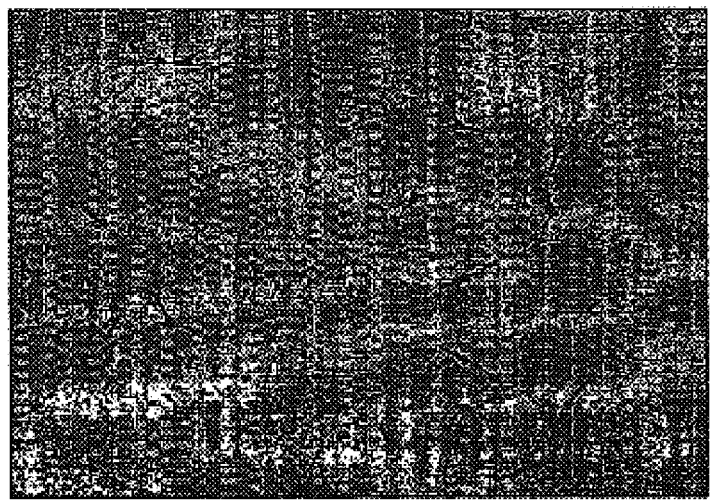
FIG. 1 illustrates the effect of SNS in inhibiting the human endothelial cell tube formation induced by fibroblast growth factor basic (FGF2).

Applicants have solved the stated problem by providing as a small recognition epitope, a three amino acid residue peptide, i.e. a tripeptide, that inhibits endothelial cell tube formation and shows inhibition of angiogenesis-mediated processes. Methods of use of the tripeptide are also provided.

The term "tripeptide" as used herein, is intended to mean a peptide having a three amino acid residues, and includes any of the analogues, peptide mimetics, and chemical derivatives discussed herein.

As used herein, the term "peptide" is intended to mean two or more amino acid residues covalently bonded together. A peptide of the invention includes polypeptides having several hundred or more amino acid residues. Usually, the covalent bond between the two or more amino acid residues is an amide bond. However, the amino acids can be joined together by various other means known to those skilled in the peptide and chemical arts. Therefore, the term "peptide" is intended to include molecules which contain, in whole or in part, non-amide linkages between the amino acids, amino acid analogues and mimetics. Similarly, the term also includes cyclic peptides and other conformationally constrained structures.

SNS and SQS Tripeptides

The tripeptide of the instant invention has three amino acid residues that render angiogenesis inhibitory action in tissue, animals, and individuals.

One preferred tripeptide of the instant invention is characterized by the sequence serine-asparagine-serine, depicted in Structure 1, also represented by Ser-Asn-Ser, also abbreviated in single letter amino acid code as and referred to hereinafter as "SNS". The preferred amino acids are levorotatory forms and the amino-terminus is capped with an acetyl group and the carboxy-terminus is capped with carboxamide.

(Structure 1)

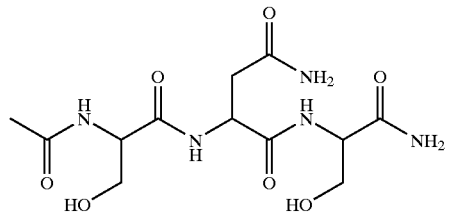

Another preferred embodiment of the instant invention is Ser-Gln-Ser, also abbreviated in single letter amino acid code as SQS, wherein the amino acids are levorotatory forms and the amino-terminus is capped with an acetyl group and the carboxy-terminus is capped with carboxamide.

Additional embodiments of the tripeptide of the instant invention are analogues, peptide mimetics, and chemical derivatives of Ser-Asn-Ser such that the tripeptide contains additional chemical moieties or modified amino acids not normally part of a naturally occurring protein, as will be discussed further herein.

The term "capped" refers to the addition of a group on the amino- or carboxy-terminus of the tripeptide. The termini of the tripeptide of the present invention are preferably blocked or "capped" with an acetyl group ($CH_3CO$—) bound to the N-terminal amino group and an amido (—$NH_2$) group bound to the C-terminal carboxyl group of the tripeptide of the invention; which is also abbreviated as "carboxamide". The tripeptide can be capped with any other group.

In this disclosure, a number of abbreviations are used. The following definitions are provided.

"Endothelial cell" is abbreviated EC.
"Fibroblast growth factor basic" is abbreviated FGF2.
"Chorioallantoic membrane" is abbreviated CAM.
"Vascular endothelial growth factor" is abbreviated VEGF.
"trans-4-Hydroxyproline" is abbreviated t4Hyp.
"1-Hydroxybenztriazole" is abbreviated HOBt.
"2-(1H-benzotriazole-1-yl)-1,1,3,3-tetramethyluronium hexafluorophosphate" is abbreviated HBTU.
"Diisopropylethylamine" is abbreviated DIEA.
"Dimethylforamide" is abbreviated DMF.
"Trifluoroacetic acid is abbreviated TFA.
"Triisopropylsilane" is abbreviated TIS.
"Human umbilical vein endothelial cells" is abbreviated HUVEC.
"Endothelial Cell Growth Medium" is abbreviated EGM.
"Endothelial Cell Basal Medium" is abbreviated EBM.
"Bovine serum albumin" is abbreviated BS.
"9-Fluorenylmethyloxycarbonyl" is abbreviated FMOC.

General Chemical Synthesis Methods

Given their short length, the tripeptides of the present invention are preferably prepared using solid-phase synthesis, such as that generally described by Chan et al., (In *FMOC Solid Phase Peptide Synthesis: A Practical Approach,* Oxford University Press; Chapter 3 (2000)), although other equivalent chemical syntheses known in the art are also useful (Merrifield, *J. Amer. Chem. Soc.* 85:2149–54 (1963)). Solid-phase peptide synthesis may be initiated from the C-terminus of the peptide by coupling a protected α-amino acid to a suitable resin. Such a starting material can be prepared by attaching an α-amino acid-protected amino acid by an ester linkage to a chloromethylated resin or to a hydroxymethyl resin, or by an amide bond to a BHA resin or MBHA resin. BHA and MBHA resin supports are commercially available and are generally used only when the desired polypeptide being synthesized has an unsubstituted amide at the C-terminus.

The amino acids can be coupled to the growing peptide chain using techniques well known in the art for the formation of peptide bonds. For example, one method involves converting the amino acid to a derivative that will render the carboxyl group of the amino acid more susceptible to reaction with the free N-terminal amino group of the growing peptide chain. Specifically, the C-terminal of the protected amino acid can be converted to a mixed anhydride by the reaction of the C-terminal with ethyl chloroformate, phenyl chloroformate, sec-butyl chloroformate, isobutyl chloroformate, or pivaloyl chloride or other similar acid chlorides. Alternatively, the C-terminal of the amino acid can be converted to an active ester, such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole. Another coupling method involves the use of a suitable coupling agent, such as N,N'-dicyclohexylcarbodiimide or N,N'-diisopropylcarbodiimide.

The α-amino group of each amino acid employed in the peptide synthesis must be protected during the coupling reaction to prevent side reactions involving their active α-amino function. Certain amino acids contain reactive side-chain functional groups (e.g., sulfhydryl, amino, carboxyl, and hydroxyl) and such functional groups must also be protected with suitable protecting groups to prevent a chemical reaction from occurring at either (1) the α-amino group site or (2) a reactive side chain site during both the initial and subsequent coupling steps.

In the selection of a particular protecting group to be used in synthesizing the peptides, the following general rules are typically followed. Specifically, an α-amino protecting group (1) should render the α-amino function inert under the conditions employed in the coupling reaction, (2) should be readily removable after the coupling reaction under conditions that will not remove side-chain protecting groups and will not alter the structure of the peptide fragment, and (3) should substantially reduce the possibility of racemization upon activation, immediately prior to coupling.

On the other hand, a side-chain protecting group (1) should render the side chain functional group inert under the conditions employed in the coupling reaction, (2) should be stable under the conditions employed in removing the α-amino protecting group, and (3) should be readily removable from the desired fully-assembled peptide under reaction conditions that will not alter the structure of the peptide chain.

It will be apparent to those skilled in the art that the protecting groups known to be useful for peptide synthesis vary in reactivity with the agents employed for their removal. For example, certain protecting groups, such as triphenylmethyl and 2-(p-biphenyl)isopropyloxycarbonyl, are very labile and can be cleaved under mild acid conditions. Other protecting groups, such as t-butyloxycarbonyl (BOC), t-amyloxycarbonyl, adamantyl-oxycarbonyl, and p-methoxybenzyloxycarbonyl, are less labile and require moderately strong acids for their removal, such as trifluoroacetic, hydrochloric, or boron trifluoride in acetic acid. Still other protecting groups, such as benzyloxycarbonyl (CBZ), halobenzyloxycarbonyl, p-nitrobenzyloxycarbonyl, and isopropyloxycarbonyl, are even less labile and require even stronger acids, such as hydrogen fluoride, hydrogen bromide, or boron trifluoroacetate in trifluoroacetic acid, for their removal.

Among the classes of amino acid protecting groups useful for protecting the α-amino group or for protecting a side chain group are included the following:

(1) For an α-amino group, three typical classes of protecting groups are:
  (a) aromatic urethane-type protecting groups, such as fluorenylmethyloxycarbonyl (FMOC), CBZ, and substituted CBZ, such as, p-chlorobenzyloxycarbonyl, p-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like;
  (b) aliphatic urethane-type protecting groups, such as BOC, t-amyloxycarbonyl, isopropyloxycarbonyl, 2-(p-biphenyl)isopropyloxycarbonyl, allyloxycarbonyl and the like; and
  (c) cycloalkyl urethane-type protecting groups, such as cyclopentyloxycarbonyl, adamantyloxycarbonyl, and cyclohexyloxycarbonyl.

The preferred α-amino protecting groups are BOC and FMOC.

(2) For the side chain amino group present in Lys, protection may be by any of the groups mentioned above in (1) such as BOC, 2-chlorobenzyloxycarbonyl and the like.

(3) For the guanidino group of Arg, protection may be provided by nitro, tosyl, CBZ, adamantyloxycarbonyl, 2,2,5,7,8-pentamethylchroman-6-sulfonyl, 2,3,6-trimethyl-4-methoxyphenylsulfonyl, or BOC groups.

(4) For the hydroxyl group of Ser or Thr, protection may be, for example, by t-butyl; benzyl (BZL); or substituted BZL, such as p-methoxybenzyl, p-nitrobenzyl, p-chlorobenzyl, o-chlorobenzyl, and 2,6-dichlorobenzyl.

(5) For the carboxyl group of Asp or Glu, protection may be, for example, by esterification using such groups as BZL, t-butyl, cyclohexyl, cyclopentyl, and the like.

(6) For the imidazole nitrogen of His, the benzyloxymethyl (BOM) or tosyl moiety is suitably employed as a protecting group.

(7) For the phenolic hydroxyl group of Tyr, a protecting group such as tetrahydropyranyl, tert-butyl, trityl, BZL, chlorobenzyl, 4-bromobenzyl, and 2,6-dichlorobenzyl are suitably employed. The preferred protecting group is bromobenzyloxycarbonyl.

(8) For the side chain amino group of Asn or Gln, xanthyl (Xan) is preferably employed.

(9) For Met, the amino acid is preferably left unprotected.

(10) For the thio group of Cys, p-methoxybenzyl is typically employed.

The first C-terminal amino acid of the growing peptide chain, e.g., Glu, is typically protected at the α-amino position by an appropriately selected protecting group such as BOC. The BOC-Glu-(γ-cyclohexyl)-OH can be first coupled to a benzylhydrylamine resin using isopropylcarbodiimide at about 25° C. for two hours with stirring or to a chloromethylated resin. Following the coupling of the BOC-protected amino acid to the resin support, the α-amino protecting group is usually removed, typically by using trifluoroacetic acid (TFA) in methylene chloride or TFA alone. The α-amino group de-protection reaction can occur over a wide range of temperatures, but is usually carried out at a temperature between about 0° C. and room temperature.

Other standard α-amino group de-protecting reagents, such as HCl in dioxane, and conditions for the removal of specific α-amino protecting groups are within the skill of those working in the art. Following the removal of the α-amino protecting group, the unprotected α-amino group, generally still side-chain protected, can be coupled in a stepwise manner in the intended sequence.

Each protected amino acid or amino acid sequence is usually introduced into the solid-phase reactor in amounts in excess of stoichiometric quantities, and the coupling is suitably carried out in an organic solvent, such as dimethylformamide (DMF), methylene chloride or mixtures thereof. If incomplete coupling occurs, the coupling procedure is customarily repeated before removal of the N-amino protecting group in preparation for coupling to the next amino acid. Following the removal of the α-amino protecting group, the remaining α-amino and side-chain-protected amino acids can be coupled in a stepwise manner in the intended sequence. The success of the coupling reaction at each stage of the synthesis may be monitored. A preferred method of monitoring the synthesis is by the ninhydrin reaction. The coupling reactions can also be performed automatically using well-known commercial methods and devices, for example, a Beckman 990 Peptide Synthesizer.

Upon completion of the desired peptide sequence, the protected peptide must be cleaved from the resin support, and all protecting groups must be removed. The cleavage reaction and removal of the protecting groups is suitably accomplished concomitantly or consecutively with de-protection reactions. When the bond anchoring the peptide to the resin is an ester bond, it can be cleaved by any reagent that is capable of breaking an ester linkage and of penetrating the resin matrix. One especially useful method is by treatment with liquid anhydrous hydrogen fluoride. This reagent will usually not only cleave the peptide from the resin, but will also remove all acid-labile protecting groups and, thus, will directly provide the fully de-protected peptide. When additional protecting groups that are not acid-labile are present, additional de-protection steps must be carried out. These steps can be performed either before or after the hydrogen fluoride treatment described above, according to specific needs and circumstances.

When a chloromethylated resin is used, the hydrogen fluoride cleavage/de-protection treatment generally results in the formation of the free peptide acids. When a benzhydrylamine resin is used, the hydrogen fluoride treatment generally results in the free peptide amides. Reaction with hydrogen fluoride in the presence of anisole and imethylsulfide at 0° C. for one hour will typically remove the side-chain protecting groups and, release the peptide from the resin.

When it is desired to cleave the peptide without removing protecting groups, the protected peptide-resin can be subjected to methanolysis, thus yielding a protected peptide in which the C-terminal carboxyl group is methylated. This methyl ester can be subsequently hydrolyzed under mild alkaline conditions to give the free C-terminal carboxyl group. The protecting groups on the peptide chain can then be removed by treatment with a strong acid, such as liquid hydrogen fluoride. A particularly useful technique for methanolysis is that in which the protected peptide-resin is treated with methanol and potassium cyanide in the presence of a crown ether.

Other methods for cleaving a protected peptide from the resin when a chloromethylated resin is employed include (1) ammoniolysis and (2) hydrazinolysis. If desired, the resulting C-terminal amide or hydrazide can be hydrolyzed to the free C-terminal carboxyl moiety, and the protecting groups can be removed conventionally. The protecting group present on the N-terminal α-amino group may be removed either before, or after, the protected peptide is cleaved from the support.

Purification of the peptides of the invention is typically achieved using chromatographic techniques, such as preparative HPLC (including reverse phase HPLC), gel permeation, ion exchange, partition chromatography, affinity chromatography (including monoclonal antibody columns), and the like, or other conventional techniques such as countercurrent distribution or the like.

The SNS tripeptides of the present invention may also be prepared using recombinant DNA technology.

Amino Acid Analogues

As used herein, the term "amino acid" is intended to mean both naturally occurring and non-naturally occurring amino acids, as well as amino acid analogues and mimetics. Naturally occurring amino acids include the 20 (L)-amino acids utilized during protein biosynthesis as well as others, such as, 4-hydroxyproline, hydroxylysine, desmosine, isodesmosine, homocysteine, citrulline and orthinine. Non-naturally occurring amino acids include, for example, (D)-amino acids, norleucine, norvaline, p-fluorophenylalanine, ethionine and the like.

As used herein, amino acid "analogues" or peptide "analogues" include modified forms of naturally and non-naturally occurring amino acids. Such modifications can include, for example, substitution or replacement of chemical groups and moieties on the amino acid or by derivitization of the amino acid.

Included in this invention are tripeptides in which at least one amino acid residue varies from the tripeptide of formula (1) (Ser-Asn-Ser). For a detailed description of protein chemistry and structure, see Schulz, G. E. et al., In *Principles of Protein Structure,* Springer-Verlag, New York, 1979, and Creighton, T. E., In *Proteins: Structure and Molecular Principles,* W. H. Freeman & Co., San Francisco, 1984. The types of substitutions which may be made in the tripeptide of formula (1) (Ser-Asn-Ser) of the present invention may be conservative substitutions and are defined herein as exchanges within one of the following groups. However, the instant invention is not limited to these substitutions.

(1) D-amino acids for L-amino acids (2) Small aliphatic, nonpolar or slightly polar residues: e.g., Ala, Ser, Thr, Gly;

(3) Polar, negatively charged residues and their amides: e.g., Asp, Asn, Glu, Gln;

(4) Polar, positively charged residues: e.g., His, Arg, Lys;

Even where it is difficult to predict the exact effect of a substitution in advance of doing so, one skilled in the art will appreciate that the effect can be evaluated by routine screening assays, preferably the biological assays described below. Modifications of peptide properties including redox or thermal stability, hydrophobicity, susceptibility to proteolytic degradation or the tendency to aggregate with carriers or into multimers are assayed by methods well known to the ordinarily skilled artisan.

Those skilled in the art know or can determine what structures constitute functionally equivalent amino acid analogues.

Chemical Derivatives

As used herein, "chemical derivatives" of the tripeptide of the present invention contain additional chemical moieties not normally a part of the tripeptide. Covalent modifications of the tripeptide are included within the scope of this invention. Such modifications may be introduced into the molecule by reacting targeted amino acid residues of the peptide with an organic derivatizing agent that is capable of reacting with selected side chains or terminal residues.

The amino and carboxyl termini are preferably blocked or "capped" with acetyl ($CH_3CO$—), bound to the amino-terminal N and amido (—$NH_2$) bound to the C-terminal carboxyl group; also abbreviated as "carboxamide", but can be readily capped with any other group. Judicious choice of capping groups allows the addition of other activities to the peptide. For example, the presence of a sulfhydryl group linked to the N- or C-terminal cap will permit conjugation of the derivatized peptide to other molecules. Some amino-terminal capping groups are compounds selected from the group consisting of acetyl, benzoyl, alkylsulfonyl, arylsulfonyl, alkylaminoacyl, arylaminoacyl, formyl, peptide and polymer. Examples of carboxy-terminal groups are compounds selected from the group consisting of $NH_2$, OH, and NHR, wherein R is selected from the group consisting of alkyl, aryl, peptide and polymer.

The capped peptides are examples of preferred chemical derivatives of the natural (L-amino acid configuration) uncapped peptide. Any of the above combination of analogues or chemical derivatives may be capped with any of the capping groups disclosed herein.

Amino Acid and Peptide Mimetics

As used herein, an "amino acid mimetics", include, for example, organic structures which exhibit functionally similar properties such as charge and charge spacing characteristic of the reference amino acid. Mimetics also include constrained structures so as to maintain optimal spacing and charge interactions of the amino acid or of the amino acid functional groups. Those skilled in the art know or can determine what structures constitute functionally equivalent amino acid mimetics.

As used herein, a "peptide mimetic" or peptidomimetic is an organic molecule that retains similar peptide chain pharmacophore groups as are present in the corresponding peptide. Peptide mimetics also can be functional equivalents of the particular peptide. The SNS tripeptides of the invention can be grouped based on the pharmacophore properties. As used herein, the term "pharmacophore" is defined as a particular arrangement of functional groups that is required for a compound to produce a particular response or have a desired activity.

A preferred peptide mimetic compound of the invention is one that mimics the biological effect of SNS, capped or uncapped. A peptidomimetic agent may be an unnatural occurring peptide (D-amino acid configuration) or a non-peptide agent which has the stereochemical properties of the tripeptide of the present invention, capped or uncapped, such that it has the binding activity or biological activity of the tripeptide of the present invention, capped or uncapped.

Peptidomimetic compounds, either agonists, substrates or inhibitors, have been described for a number of bioactive peptides such as opioid peptides, VIP, thrombin, HIV protease, etc. Methods for designing and preparing peptidomimetic compounds are known in the art (Kempf, D. J. *Methods Enzymol.* 241:334–354 (1994); Hruby, V. J., *Biopolymers* 33:1073–82 (1993); Wiley et al., *Med. Res. Rev.* 13:327–384 (1993); Claeson, G., *Blood Coagul. Fibrinolysis* 5:411–436 (1994)). These methods may be used to prepare capped or uncapped peptidomimetics which possess at least the binding capacity and specificity of the tripeptide and preferably also possess the biological activity. Knowledge of peptide chemistry and general organic chemistry available to those skilled in the art are sufficient for the design and testing of such compounds.

For example, such peptidomimetics may be identified by inspection of the cystallographically-derived three-dimensional structure of a peptide of the invention. Alternatively, the structure of a tripeptide of the invention bound to its receptor(s) can be gained by the techniques of nuclear magnetic resonance spectroscopy. The better knowledge of the stereochemistry of the interaction of, for example, SNS, capped or uncapped, with its receptor will permit the rational design of such peptidomimetic agents.

Angiogenesis and Angiogenesis-Dependent Diseases

As used herein, the terms "angiogenesis inhibitory", "angiogenesis inhibiting" or "anti-angiogenic" include vasculogenesis, and are intended to mean effecting a decrease in the extent, amount, or rate of neovascularization. Effecting a decrease in the extent, amount, or rate of endothelial cell proliferation or migration in the tissue is a specific example of inhibiting angiogenesis.

The term "angiogenesis inhibitory composition" refers to a composition which inhibits angiogenesis-mediated processes such as endothelial cell migration, proliferation, tube formation and subsequently leading to the inhibition of the generation of new blood vessels from existing ones, and consequently the inhibition of angiogenesis-dependent diseases.

As used herein, the term "angiogenesis-dependent disease" is intended to mean a disease where the process of angiogenesis or vasculogenesis sustains or augments a pathological condition. Angiogenesis is the formation of new blood vessels from pre-existing capillaries or post-capillary venules. Vasculogenesis results from the formation of new blood vessels arising from angioblasts which are endothelial cell precursors. Both processes result in new blood vessel formation and are included in the meaning of the term angiogenesis-dependent diseases. Similarly, the term "angiogenesis" as used herein is intended to include de novo formation of vessels such as that arising from vasculogenesis as well as those arising from branching and sprouting of existing vessels, capillaries and venules.

Angiogenesis, including vasculogenesis, is an important physiological process, without which embryonic development and wound healing would not occur. However, angiogenesis is also inappropriately recruited into numerous pathological conditions as a means to provide adequate blood and nutrient supply to the cells within the affected tissue. Many of these pathological conditions involve abberant cell proliferation or regulation. Such conditions in which angiogenesis is believed to be important are referred to herein as angiogenesis-dependent diseases. However, methods of the invention also can be used beneficially to inhibit angiogenesis associated with normal physiological processes. For example, the inhibition of angiogenesis associated with the menstrual cycle can be prophylactically used as an effective method of birth control. Therefore, the description below in reference to the treatment of angiogenesis-dependent diseases are also applicable to the inhibition of normal angiogenic responses where a prophylactic or therapeutic need or benefit exists.

Angiogenesis-dependent desease include, for example, inflammatory disorders such as immune and non-immune inflammation, rheumatoid arthritis, chronic articular rheumatism and psoriasis; disorders associated with inappropriate or inopportune invasion of vessels such as diabetic retinopathy, neovascular glaucoma, retinopathy of prematurity, macular degeneration, corneal graft rejection, retrolental fibroplasia, rubeosis, capillary proliferation in atherosclerotic plaques and osteoporosis; and cancer associated disorders, including for example, solid tumors, tumor metastases, blood born tumors such as leukemias, angiofibromas, Kaposi sarcoma, benign tumors such as hemangiomas, acoustic neuromas, neurofibromas, trachomas, and pyogenic granulomas, as well as other cancers which require neovascularization to support tumor growth. Additional examples of angiogenesis-dependent diseases include, for example, Osler-Webber Syndrome; myocardial angiogenesis; plaque neovascularization; telangiectasia; hemophiliac joints and wound granulation. Other diseases in which angiogenesis plays a role in the maintenance or progression of the pathological state are known to those skilled in the art and are similarly intended to be included within the meaning of the term used herein.

In Vitro Biological Assay of Angiogenesis Inhibiting Activity

The compounds of the instant invention were tested for their angiogenesis inhibiting activity in several assay systems in vitro. Endothelial cells, for example, human umbilical vein endothelial cells (HUVEC) or human microvascular endothelial cells (HMVEC) which can be prepared or obtained commercially, were mixed at a concentration of $2\times10^5$ cells/mL with fibrinogen (5 mg/mL in phosphate buffered saline (PBS) in a 1:1 (v/v) ratio. Thrombin was added (5 units/mL final concentration) and the mixture was immediately transferred to a 24-well plate (0.5 mL per well). The fibrin gel was allowed to form and then vascular endothelial growth factor (VEGF) and fibroblast growth factor basic (FGF2) were added to the wells (each at 5 ng/mL final concentration) along with the test compound. The cells were incubated at 37° C. in 5% $CO_2$ for 4 days at which time the cells in each well were counted and classified as either rounded, elongated with no branches, elongated with one branch, or elongated with 2 or more branches. Results are expressed as the average of 5 different wells for each concentration of compound. Typically, in the presence of angiogenic inhibitors, cells remain either rounded or form undifferentiated tubes (e.g., 0 or 1 branch). This assay is recognized in the art to be predictive of angiogenic efficacy (or angiogenesis inhibiting activity) in vivo (Grant et al., *In Vitro Cell Dev. Biol.* 27A:327–336 (1991); Min et al., *Cancer Res.* 56:2428–2433 (1996)).

In an alternate assay, endothelial cell tube formation is observed when endothelial cells are cultured on Matrigel® matrix-coated plates, commercially available from Becton Dickinson of Bedford, Pa. (Schnaper et al., *J. Cell. Physiol.* 165:107–118 (1995)). Endothelial cells ($1\times10^4$ cells/well) are transferred onto Matrigel® matrix-coated 24-well plates, and tube formation is quantitated after 48 hours. Inhibitors are tested by adding them either at the same time as the endothelial cells or at various time points thereafter.

This assay models angiogenesis by presenting to the endothelial cells a particular type of basement membrane, namely the layer of matrix which migrating and differentiating endothelial cells might be expected to first encounter. In addition to bound growth factors, the matrix components found in Matrigel® matrix (and in basement membranes in situ) or proteolytic products thereof may also be stimulatory for endothelial cell tube formation which makes this model complementary to the fibrin gel angiogenesis model.

Additionally, angiogenic activities of compounds of the present invention were evaluated by the chick chorioallantoic membrane (CAM) assay (Oikawa et al., *Cancer Lett.* 59:57–66 (1991)).

Methods of Administration

The invention provides a method of inhibiting angiogenesis in tissue by administering an angiogenesis-inhibitory amount of the SNS tripeptide, an analogue, a mimetic or a chemical derivative thereof.

The invention further provides a method of treating an angiogenesis-dependent disease in an animal by administering an angiogenesis inhibitory amount of the SNS tripeptide, an analogue or a functional equivalent thereof.

The invention also provides a method of inhibiting agiogenesis-dependent disease in a human by administering an angiogenesis inhibitory amount of the SNS tripeptide, an analogue or a functional equivalent thereof.

The SNS tripeptide, its analogues, or chemical derivatives, can be administered to a tumor bearing animal to determine the inhibiting activity or efficacy of the peptide on tumor growth, compared to a non-anti-angiogenesis peptide control. A decrease in the rate or extent of tumor growth, or a disappearance of the tumor correlates with the anti-angiogenic activity and efficacy against progression of an angiogenesis-dependent disease. For a description of tumor bearing animal models see, for example, U.S. Pat. No. 5,639,725, which is hereby incorporated by reference.

Dosage of Administration

In determining the activity of and/or efficacy of the SNS tripeptide, analogue or chemical derivative in any of the above methods, the peptide can be administered within a concentration range known in the art to be indicative of an inhibitor's activity in a particular assay. For example, a concentration of a polypeptide inhibitor which yields indicative results in the bovine capillary endothelial cell assay is generally about 100–1000 ng/ml. Similarly, the concentration of a polypeptide inhibitor which would yield a positive result for a polypeptide inhibitor that is active against angiogenesis in a CAM is generally about, for example, 0.5–20 µg/ml, 10–20 µg/disc, over a range of concentrations of 0.1–100 µg/disc, or 25 µg/disc. An indicative concentration for a polypeptide inhibitor which would be expected to yield positive results in the rabbit corneal assay is generally about 40 µg/hydron pellet. Finally, concentrations for polypeptide inhibitors which would yield indicative results in the tumor metastasis and tumor bearing animal models described above are about 250 µg twice weekly or 10 mg/kg/day for 10 days; and 12.5 µg daily or 1 mg twice a week, respectively. Further refinement can be performed by, for example, varying the concentration of the SNS tripeptide within the active concentration range to determine an optimal concentration or amount for inhibiting angiogenesis.

Moreover, the above described models, as well as other methods known to those skilled in the art, can similarly be used to determine appropriate dosage regimes in regard to timing of administrations, number of administrations and amount per administration of SNS tripeptide, analogue, mimetic or chemical derivative to inhibit or to treat an angiogenesis-dependent disease. Similarly, the above described methods also can be routinely used to make and identify new, modified or improved SNS tripeptides, analogues, mimetics or chemical derivatives. Given the teachings and guidance described herein, those skilled in the art will know or can determine an effective amount of the SNS tripeptide, analogue, mimetic or chemical derivative to inhibit angiogenesis-dependent or to treat an angiogenesis-dependent disease.

As used herein, the term "angiogenesis inhibitory amount" is intended to mean an amount of an SNS tripeptide, analogue, mimetic or chemical derivative of the invention required to effect a decrease in the extent, amount or rate of neovascularization when administered to a tissue, animal or individual. The dosage of an SNS tripeptide, analogue, mimetic or chemical derivative required to be therapeutically effective will depend, for example, on the angiogenesis-dependent disease to be treated, the route and form of administration, the potency and big-active half-life of the molecule being administered, the weight and condition of the tissue, animal or individual, and previous or concurrent therapies. The appropriate amount application of the method can be determined by those skilled in the art, using the guidance provided herein. For example, the amount can be extrapolated from in vitro or in vivo angiogenesis assays described above. One skilled in the art will recognize that the condition of the patient needs to be monitored throughout the course of therapy and that the amount of the composition administered can be adjusted accordingly.

For inhibiting angiogenesis or treating an angiogenesis-dependent disease, an angiogenesis inhibitory amount of a peptide of the invention can be, for example, between about 10 μg/kg to 500 mg/kg body weight, for example, between about 0.1 mg/kg to 100 mg/kg, or preferably between about 1 mg/kg to 50 mg/kg, depending on the treatment regimen. For example, if a peptide is administered from one to several times a day, then a lower dose would be needed than if a peptide were administered weekly, or monthly or less frequently. Similarly, formulations that allow for timed-release of a peptide would provide for the continuous release of a smaller amount of a peptide than would be administered as a single bolus dose. For example, a peptide can be administered at 4 mg/kg/week.

Delivery Systems

The SNS tripeptide, analogue, mimetic or chemical derivative of the invention can be delivered systemically, such as intravenously or intraarterially. An SNS tripeptide, analogue, mimetic or chemical derivative can also be administered locally at a site of angiogenesis. Appropriate sites for administration of SNS tripeptide, analogue, mimetic or chemical derivative are known or can be determined by those skilled in the art depending on the clinical indications of the individual being treated. For example, the SNS tripeptides, analogues, mimetics or chemical derivatives, having inhibitory activity, described above can be provided as isolated and substantially purified proteins and protein fragments as well as insoluble aggregate in pharmaceutically acceptable formulations using formulation methods known to those of ordinary skill in the art. These formulations can be administered by standard routes, including for example, topical, transdermal, intranasal, intraperitoneal, intracranial, intracerebroventricular, intracerebral, intravaginal, intrauterine, oral, rectal or parenteral (e.g., intravenous, intraspinal, subcutaneous or intramuscular) routes. In addition, an SNS tripeptide, analogue, mimetic or chemical derivative can be incorporated into biodegradable polymers allowing for sustained release of the compound, the polymers being implanted in the vicinity of where drug delivery is desired, for example, at the site of a tumor or implanted so that the SNS tripeptide, analogue, mimetic or chemical derivative is released systemically over time. Osmotic minipump peptides, analogues, mimetics or chemical derivatives can also be used to provide controlled delivery of high concentrations of SNS tripeptide, analogue, mimetic or chemical derivative through cannulae to the site of interest, such as directly into a metastatic growth or into the vascular supply of a tumor. The biodegradable polymers and their use are described, for example, in detail in Brem et al: J. Neurosurg 74:441–446 (19911, which is incorporated herein by reference.

The SNS tripeptide, analogue, mimetic or chemical derivative can also be administered in conjunction with with an additional therapeutic compound selected from the group consisting of chemotherapeutics, antibiotics, antivirals, antiinflammatories, targeting compounds, cytokines, immunotoxins, anti-tumor antibodies, angiogenic inhibitors, anti-edema agents, radiosensitizers and combinations thereof.

The invention provides compositions of SNS tripeptide, analogue, mimetic or chemical derivative together with a pharmaceutically acceptable medium and formulations. Such compositions can be used in a method of the invention to inhibit angiogenesis or treat an angiogenesis-dependent disease. For example, an SNS tripeptide, analogue, mimetic or chemical derivative can be administered as a solution or suspension together with a pharmaceutically acceptable medium. Such a pharmaceutically acceptable medium can be, for example, water, sodium phosphate buffer, phosphate buffered saline, normal saline or Ringer's solution or other physiologically buffered saline, or other solvent or vehicle such as a glycol, glycerol, an oil such as olive oil or an injectable organic ester.

The SNS tripeptide, analogue, mimetic or chemical derivative formulations include those applicable for parenteral administration such as subcutaneous, intraperitoneal, intramuscular, intravenous, intradermal, intracranial, intratracheal, and epidural administration. As well as formulations applicable for oral, rectal, ophthalmic (including intravitreal or intracameral), nasal, topical (including buccal and sublingual), intrauterine, or vaginal administration. The SNS tripeptide, analogue, mimetic or chemical derivative formulations can be presented in unit dosage form and can be prepared by pharmaceutical techniques well known to those skilled in the art. Such techniques include the step of bringing into association the active ingredient and the pharmaceutical carrier(s) or excipient(s). The SNS tripeptide, analogue, mimetic or chemical derivative of the invention also can be delivered to an individual for inhibiting angiogenesis or treating an angiogenesis-dependent disease by administering an encoding nucleic acid for the peptide. Therefore, the encoding nucleic acids for the SNS tripeptides, analogues, mimetics and chemical derivatives of the invention are useful in conjunction with a wide variety of gene therapy methods known in the art for delivering an angiogenesis inhibitory amount of the peptide or variant. Using the teachings and guidance provided herein, encoding nucleic acids for one or more SNS tripeptides, analogues, mimetics, chemical derivatives or a combination thereof can be incorporated into a vector or delivery system known in the art and used for delivery and expression of the encoding sequence to achieve an angiogenesis inhibitory amount. Applicable vector and delivery systems known in the art include, for example, retroviral vectors, adenovirus vectors, adenoassociated virus, ligand conjugated particles and nucleic acids for targeting, isolated DNA and RNA, liposomes, polylysine, and cell therapy, including hepatic cell therapy, employing the transplantation of cells modified to express SNS tripeptides, as well as various other gene delivery methods and modifications known to those skilled in the art, such as those described in Shea et al., *Nature Biotechnol.* 17:551–559 (1999), which is incorporated herein by reference.

Specific examples of methods well known in art are described in, for example, U.S. Pat. No. 5,399,346; U.S. Pat. Nos. 5,580,859; 5,589,466; 5,460,959; 5,656,965; 5,643,578; 5,620,896; 5,460,959; 5,506,125; European Patent Application No. EP 0 779 365 A2; PCT No. WO 97/10343; PCT No. WO 97/09441; PCT No. WO 97/10343, all of which are incorporated herein by reference. Other methods known to those skilled in the art also exist and are similarly applicable for the delivery of an angiogenesis inhibitory amount of an SNS tripeptide, analogue, mimetic or chemical derivative by expressing the encoding nucleic acid sequence.

The present invention also relates to encoding nucleic acids and vectors useful in the gene therapy methods and can be prepared by methods known in the art. Compositions containing such nucleic acids, vectors and pharmaceutically acceptable medium are also provided. The pharmaceutically acceptable medium should not contain elements that would degrade the desired nucleic acids. The methods of using SNS tripeptides, analogues, mimetics or chemical derivatives can employ any of the various species of SNS tripeptides, analogues, mimetics and chemical derivatives previously set forth.

Non-SNS sequences can impart structural or functional characteristics onto the peptides of the invention. Targeting of an SNS tripeptide, analogue, mimetic or chemical derivative to the site of aberrant angiogenesis confers the additional therapeutic advantage of anchoring the peptide at the site of the pathological condition. This result therefore sustains a high effective concentration of the peptide diffusible into the angiogenic area over time and essentially allows for continuous local administration of SNS tripeptide, analogue, mimetic or chemical derivative to the site of angiogenesis.

Additionally, two or more SNS tripeptides, analogues, mimetics or chemical derivatives of the invention can be administered in the methods of the invention to inhibit angiogenesis or to treat an angiogenesis-dependent disease. Similarly, one or more SNS tripeptides, analogues, mimetics or chemical derivatives can be administered in combination with one or more SNS tripeptides, analogues, mimetics or chemical derivatives to inhibit angiogenesis or treat an angiogenesis-dependent disease. Therefore, various combinations and permutations of SNS tripeptides, SNS analogues, SNS mimetics and SNS chemical derivatives and combinations thereof can be administered in the methods of the invention for the effective inhibition of angiogenesis and treatment of an angiogenesis-dependent disease.

SNS tripeptides, analogues, mimetis and chemical derivatives and combinations thereof can also be delivered in alternating administrations so as to combine their angiogenic inhibiting effects over time. For example, an SNS analogue can be administered in a single bolus dose followed by multiple administrations of one or more SNS tripeptides alone or in combination with an SNS tripeptide, analogue, mimetic or chemical derivative. Whether simultaneous or alternating delivery of the SNS tripeptide, analogue, mimetic, chemical derivative or combination thereof, the mode of administration can be any of those types of administrations described previously and will depend on the particular therapeutic need and efficacy of the SNS tripeptide, analogue, mimetic or chemical derivative selected for the purpose. Determining which species of SNS tripeptide, analogue, mimetic or chemical derivative to combine in a cocktail or to combine in a temporally administered regime, will depend on the angiogenesis-dependent disease and the specific physical characteristics of the individual affected with the disease. Those skilled in the art will know or can determine a specific cocktail or regime of administration which is effective for a particular application using the teachings and guidance provided herein together with diagnostic and clinical criteria known within the field of art of the particular angiogenesis-dependent disease.

Therapeutic Applications

The methods of inhibiting angiogenesis or treating angiogenesis-dependent disease by administering SNS tripeptide, analogue, mimetic or chemical derivative additionally can be practiced in conjunction with other therapies. Possible embodiments of the invention contemplate use of such administration in conjunction with other therapies such as conventional chemotherapy directed against solid tumors and for the control of establishment of metastases. The administration of angiogenesis inhibitor is typically conducted during or after chemotherapy at time where the tumor tissue should respond to toxic assault by inducing angiogenesis to recover by the provision of a blood supply and nutrients to the tumor tissue. Additionally, it is preferred to administer such angiogenesis inhibition procedures after surgery where solid tumors have been removed as a prophylaxis against metastases.

The present composition can be used as well in conjunction with other angiogenesis inhibitors. Angiogenic inhibitors are known in the art and can be prepared by known methods. For example, angiogenic inhibitors include integrin inhibitory compounds such as $\alpha v$ integrin inhibitory antibodies, cell adhesion proteins or functional fragments thereof which contain a cell adhesion binding sequence. Additional angiogenic inhibitors include, for example, angiostatin, functional fragments of angiostatin, endostatin, fibroblast growth factor (FGF) inhibitors, FGF receptor inhibitors, VEGF inhibitors, VEGF receptor inhibitors, vascular permeability factor (VPF) inhibitors, VPF receptor inhibitors, thrombospondin, platelet factor 4, interferon-alpha, interferon-gamma, interferon-inducible protein 10, interleukin 12, gro-beta, and the 16 kDa N-terminal fragment of prolactin, thalidomide, and other mechanisms for the inhibition of angiogenesis.

Angiostatin is the subject matter of U.S. Pat. No. 5,639,725, supra. Endostatin is the subject matter of PCT publication WO 97/15666, supra. For a description of the remaining angiogenic inhibitors and targets set forth above, see for example, Chen et al., *Cancer Res.* 55:4230–4233 (1995); Good et al., *Proc. Natl. Acad. Sci. USA* 87:6629–6628 (1990); O'Reilly et al., *Cell* 79:315–328 (19943; Parangi et al., *Proc. Natl. Acad. Sci. USA* 93:2002–2007 (1996); Rastinejad et al., *Cell* 56:345–355 (1989); Gupta et al., *Proc. Natl. Acad. Sci. USA* 92:7799–7803 (1995); Maione et al., *Science* 247:77–79 (1990): Angiolillo et al., *J. Exp. Med.* 182:155–162 (1995); Strieter et al., *Biochem. Biophys. Res. Comm.* 210:51–57 (1995); Voest et al., *J. Natl. Cancer Inst.* 87:581–586 (1995); Cao et al., *J. Exp. Med.* 182:2069–2077 (1995); Clapp et al., *Endocrinology* 133:1292–1299 (1993), respectively. For a description of additional angiogenic inhibitors see, for example, Blood et al., *Bioch. Biophys Acta.*, 1032:89–118 (1990); Moses et al., *Science,* 248:1408–1410 (1990); Ingber et al., *Lat Invest.,* 59:44–51 (1988) and U.S. Pat. Nos. 5,092,885; 5,112,946;

Formulation

Formulations suitable for parenteral administration include aqueous and non-aqueous sterile injection solutions such as the pharmaceutically acceptable mediums described above. The solutions can additionally contain, for example, anti-oxidants, buffers, bacteriostats and solutes which render the formulation isotonic with the blood of the intended recipient. Other formulations include, for example, aqueous and non-aqueous sterile suspensions which can include suspending agents and thickening agents. The formulations can be presented in unit-dose or multi-dose containers, for example, sealed ampules and vials, and can be stored in a lyophilized condition requiring, for example, the addition of the sterile liquid carrier, immediately prior to use. Extemporaneous injection solutions and suspensions can be prepared from sterile powders, granules and tablets of the kind previously described.

A pharmaceutically acceptable medium can additionally contain physiologically acceptable compounds that act, for example, to stabilize or increase the absorption of the SNS tripeptide, analogue, mimetic or chemical derivative. Such physiologically acceptable compounds include, for example, carbohydrates such as glucose, sucrose or dextrans; antioxidants such as ascorbic acid or glutathione; chelating agents such as EDTA, which disrupts microbial membranes; divalent metal ions such as calcium or magnesium; low molecular weight proteins; lipids or liposomes; or other stabilizers or excipients. An SNS tripeptide, analogue, mimetic or chemical derivative can also be formulated with a pharmaceutically acceptable medium such as a biodegradable polymer.

Polymeric Formulations

Also contemplated by this invention is the use of the angiogenesis-inhibitory tripeptides, analogues, mimetics or chemical derivatives in polymeric formulations. The tripeptides can be covalently attached by surface grafting, co-polymerization, non-covalently incorporation into a matrix or otherwise encapsulating as biomedical materials. Modulation, and control of new blood vessel formation is an essential part of approaches to tissue engineering materials where a balance of pro-antiangiogenic and anti-angiogenic factors must be maintained. The tripeptides may be used in conjuction with known promoters of angiogenesis, functional biomedical materials such as implant and prosthetic materials, scaffolds for tissue engineering, wound healing materials, ex vivo artificial organ materials, that modulate new blood vessel formation in tissue. The polymeric formulations may also be used for sustained release of the antiangiogenesis-inhibitory peptides for inhibition of new blood vessel formation. This is one example of a drug delivery method involving conjugation of the antiangiogenesis-inhibitory peptide to a carrier material that can be used to locally deliver the antiangiogenic effects of such a formulation in angiogenesis-dependent diseases.

EXAMPLES

Having now generally described the invention, the same will be more readily understood through reference to the following examples which are provided by way of illustration, and are not intended to be limiting of the present invention, unless specified.

General Methods

Chemicals

All reagents were chemical grade and purchased from Sigma Chemical Co. (St. Louis, Mo.) or through VWR Scientific (Bridgeport, N.J.). Cortisone acetate, bovine serum albumin (BSA) and gelatin solution (2% type B from bovine skin) were purchased from Sigma Chemical Co. M199 growth medium with Earl's salts, basic FGF, Insulin-Transferrin-Selenium-G Supplement (I-T-Se) 100×, Dulbecco's phosphate buffered salt solution (PBS) with and without $Ca^{+2}$ and $Mg^{+2}$ and 0.5 M EDTA were obtained from Gibco BRL (Grand Island, N.Y.). Human umbilical vein endothelial cells (HUVEC), Endothelial cell basal medium (serum-free, EBM), EGM (supplemented with growth factors, fetal calf serum), and 0.025% trypsin/0.01% EDTA solution were purchased from Clonetics Inc. (San Diego, Calif.). Human prostrate (TSU-Pr) tumor cells were obtained from American Type Culture Collection (Rockville, Md.). Matrigel® matrix and human collagen type III were purchased from Becton Dickinson (Bedford, Mass.). HEMA-3 fixative and staining solutions were purchased from Biochemical Sciences, Inc. (Swedesboro, N.J.). Fertilized chicken eggs were purchased from Charles River Laboratories, SPAFAS Avian Products & Services (North Franklin, Conn.).

Peptide Synthesis

All peptides described were prepared via standard solid-phase synthesis protocols using FMOC chemistry (Chan et al., In *FMOC Solid Phase Pepetide Synthesis: A Practical Approach*, Oxford University Press; Chapter 3 (2000)). The solid-phase, high load PAL-PEG-PS resin and all of the FMOC-protected amino acids were obtained from Perseptive Biosystems (Framingham, Mass.). Peptide synthesis involves three steps:

(1) amino acid coupling: 1-hydroxybenztriazole (HOBt)/2-(1H-benzotriazole-1-yl)-1,1,3,3-tetramethyluronium hexafluorophosphate (HBTU)/diisopropylethylamine (DIEA), (4.0/4.0/8.0 equivalents based on resin loading) and FMOC-protected amino acids (4.0 equivalents) in dimethylforamide (DMF) at room temperature for 4.0 h;

(2) FMOC deprotection: 20%v piperidine in DMF for 1.5 h;

(3) cleavage from resin: 95:5 trifluoroacetic acid (TFA)/triisopropylsilane (TIS) at room temperature for 6 h. Crude products were triturated with ethyl ether and lyophilized from aqueous solution. Molecular weights of all peptides were confirmed by electrospray mass spectrometry (MW=347.32, Obs. M+1=348.23). The structure and purity assessment of N-acetyl-serine-asparagine-serine-(Ac-Ser-Asn-Ser-carboxamide (1)) was done by inspection of the $^1$H NMR spectrum and by HPLC, where purity was estimated to be approximately 80%. Major contaminants are polyethylene glycol residue from the PAL-PEG-PS resin ($^1$H NMR spectrum peak at 63.6 ppm). The larger peptides, Ac-Asn-Tyr-Tyr-Ser-Asn-Ser (SEQ ID NO:2), Ac-Ser-Asn-Ser-Tyr-Ser-Phe-Trp-Leu (SEQ ID NO:3) and Ac-Cys-Asn-Tyr-Tyr-Ser-Asn-Ser-Tyr-Ser-Phe-Trp-Leu (SEQ ID NO:4) were prepared using the same peptide synthesis methods.

Synthesis of SNS Analogue Libraries

General

Synthesis of the library was carried out in Quest 210 synthesizer using 5 mL Teflon® reaction tubes (registered trademark of E. I. de Nemours and Company of Wilmington, Del.). Solid phase peptide synthesis was performed using the FMOC method on Argogel Rink resin. Repetitive cycles of deprotection and coupling were performed until the desired length peptide was formed. The peptides were then acylated and cleaved from the resin.

Procedure

Deprotection

Argogel Rink-FMOC (200 mg, 0.064 mmol) was weighed into a 5 mL reaction vessel and washed with 3 mL DMF. A solution of 20% piperidine/DMF (4 mL) was added and the resin was agitated for 2 minutes. The reaction mixture was filtered and the procedure repeated with fresh 4 mL aliquot of 20% piperidine solution for an additional 20 minutes. The resin was then drained and washed with 5 mL DMF four times. A 5 minute agitation was used during each wash step.

Coupling

To the reaction vessel were added 0.6 mL dry DMF, followed by 3 equivalents each of the first N-FMOC-amino acid and 1-hydroxybenzotraizole (HOBt) as a 0.5 M solution in dry DMF. The resin was agitated for 1 minute followed by the addition of 3 equivalents of HBTU as a 0.5 M solution in dry DMF. The resin was agitated for 4 hours then drained and washed 5× with 4 mL DMF, again employing a 5 minutes agitation per wash.

The deprotection procedure and coupling procedure were repeated for the second and third FMOC-amino acids. After the third amino acid was coupled, it was again subjected to the deprotection procedure.

Acylation

The resin from the above procedures was treated with 3 mL of a 1:1:2 mixture of acetic anhydride:diisopropylethylamine:DMF for 1 hour. The resin was drained and washed repeatedly with DMF.

Cleavage

To the resin were added 3 mL of 50% TFA/methylene chloride solution. The resin was agitated for 1 hour. The resin was filtered and the filtrate collected. The filtrate was added slowly to ice cold ether, causing precipitation of the desired product. The precipitate was collected by filtration and dissolved in 50% acetonitrile solution. The solution was lyophilized to give the desired product as a solid.

The meaning of abbreviations is as follows: "sec" means second(s), "min" means minute(s), "h" means hour(s), "d" means day(s), "μL" means microliter(s), "mL" means milliliter(s), "L" means liters, "mM" means millimolar, "M" means molar and "mmol" means millimole(s).

EXAMPLE 1

Inhibition of Endothelial Cell Tube Formation

Differentiation by endothelial cells was examined using a method developed by Grant et al. (*In Vitro Cell Dev. Biol.* 27A:327–336 (1991)). Matrigel® matrix, phenol-red free (commercially available from Becton Dickinson, Bedford, Mass.) was thawed overnight at 4° C. Using cold pipette tips, 3.0 mg/well of Matrigel® matrix was placed in a cold twenty-four-multiwell plate (Falcon). Matrigel® matrix was allowed to polymerize during incubation at 37° C. for 30 min.

Human umbilical vein endothelial cells (HUVEC) were maintained at 37° C. with 5% $CO_2$ and 95% humidity in endothelial cell growth medium with 2% fetal bovine serum (EGM). Tube assay was performed in endothelial cell basal medium (EBM) supplemented with 0.5% bovine serum albumin (BSA) and 1:100 diluted Insulin-Transferrin-Selenium-G supplement (I-T-Se, 100×). HUVEC were trypsinized and centrifuged and subsequently, washed twice in phosphate buffered saline (PBS). After counting, cell density was adjusted to 35,000 cells/mL.

At final concentration of 35,000 cells/mL/well were treated with recombinant human fibroblast growth factor basic (FGF2) at 100 ng/mL and peptides (see below) dissolved in EBM medium at to a concentration of 0.015 μmol. Treated cells were incubated overnight at 37° C. with 5% $CO_2$ and 95% humidity to allow cell attachment.

Subsequently, the medium was aspirated and cells were fixed and stained using a modified HEMA-3 stain kit. Digital images of microtiter well sections were collected using a DKC5000 3-CCD color video camera system (Toshiba America, New York, N.Y.) and analyzed with the Image-Pro Plus software (Media Cybernetics, Silver Spring, Md.). The area and major axis length of stained cells having a tubular morphology on the Matrigel® matrix surface (Becton Dickinson, Bedford, Pa.) counted from 5 images/well.

Figure 1B:
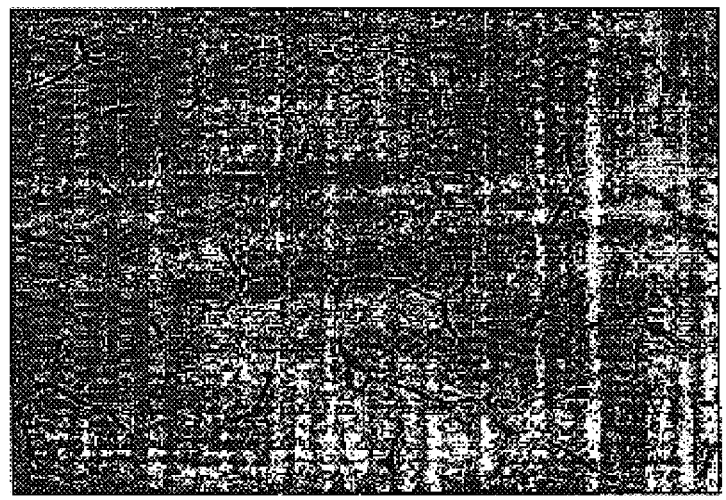
Figure 1C:
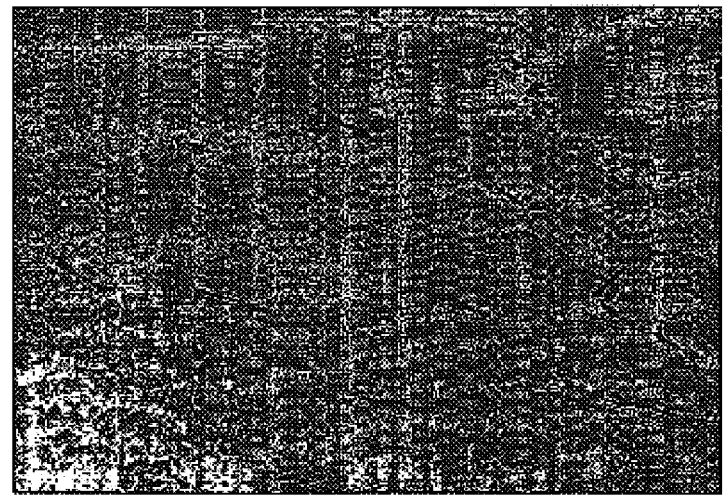

The following four peptides were tested: acetyl-Ser-Asn-Ser-carboxamide (Structure 1), acetyl-Asn-Tyr-Tyr-Ser-Asn-Ser (SEQ ID NO:2), acetyl-Ser-Asn-Ser-Tyr-Ser-Phe-Trp-Leu (SEQ ID NO:3) and acetyl-Cys-Asn-Tyr-Tyr-Ser-Asn-Ser-Tyr-Ser-Phe-Trp-Leu (SEQ ID NO:4). Table 1 and FIG. 1 clearly illustrate that acetyl-Ser-Asn-Ser-carboxamide (Structure 1) is a very potent inhibitor of FGF2-stimulated EC tube formation in vitro. Area data is expressed in units of $10^4$ square microns and length data is expressed as length/area in units of $mm/mm^2$.

TABLE 1

Microscopic Analysis of EC Tube Formation

| Sample | Concentration | Cell Tube Formation (area) | Cell Tube Formation (length) |
|---|---|---|---|
| PBS | — | 1.0554 +/− 0.11 | 41.3611 +/− 2.61 |
| FGF2 | 100 ng/mL | 2.2501 +/− 0.28 | 79.8272 +/− 8.66 |
| acetyl-SNS-carboxamide | 0.015 μmol | 1.1011 +/− 0.12 | 47.5267 +/− 4.31 |

Table 2 illustrates that acetyl-Ser-Asn-Ser-carboxamide (Structure 1) was a more potent inhibitor of FGF2-stimulated EC tube formation in vitro than the larger peptides. Percent inhibition data is expressed as the quotient of the experimental value minus the negative control value (EBM medium) divided by the difference between the positive control value and the negative control value.

TABLE 2

Average % Inhibition of EC Tube Formation by Peptides

| Sample | MW | 0.015 μmol | % inhibition cell tube formation (area) | % inhibition cell tube formation (length) |
|---|---|---|---|---|
| acetyl-SNS-carboxamide | 347.33 | 5.20 μg | 97% +/− 8 | 84% +/− 9 |
| SEQ ID NO: 3 | 787.79 | 11.80 μg | 75% +/− 7 | 65% +/− 3 |
| SEQ ID NO: 4 | 1044.14 | 15.65 μg | 71% +/− 6 | 54% +/− 3 |
| SEQ ID NO: 5 | 1587.74 | 23.8 μg | 55% +/− 2 | 49% +/− 1 |

EXAMPLE 2

Neovascularization on the CAM and Microscopic Analysis of CAM Sections

In vivo neovascularization was examined by the method previously described by Auerbach et al. (*J. Dev. Biol.* 41:391–394 (1974)). Ten-day old embryos were purchased from Spafas, Inc. (Preston, Conn.) and were incubated at 37° C. with 55% relative humidity. In the dark with the help of a candling lamp a small hole was punctured in the shell concealing the air sac with a hypodermic needle. A second hole was punctured in the shell on the broadside of the egg directly over an vascular portion of the embryonic membrane, as observed during candling. A false air sac was created beneath the second hole by the application of negative pressure to the first hole, which caused the chorioallantoic membrane (CAM) to separate from the shell. A window, approximately $1.0 \, cm^2$, was cut in the shell over the dropped CAM with the use of a small crafts grinding wheel (Dremel, Division of Emerson Electric Company Racine, WI) which allowed direct access to the underlying CAM. Filter disks of #1 filter paper (Whatman International, United Kingdom) were soaked in 3 mg/mL cortisone acetate (Sigma, St. Louis, Mo.) in a solution of 95% ethanol and water and subsequently air dried under sterile conditions. FGF2 (Life Technologies, Gaithersburg, Md.) was used to grow vessels on the CAMs of 10-d old chick embryos. Sterile filter disks adsorbed with FGF2 dissolved in PBS at 1 µg/mL were placed on growing CAMs. At 24 h, test compounds or control vehicle was added directly to CAMs topically.

Figure 2A:
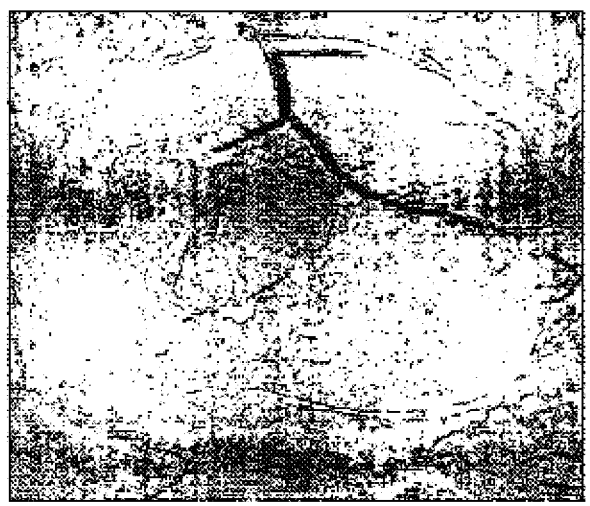
FIG. 2 illustrates the effect of SNS in inhibiting FGF2-induced angiogenesis in the chorioallantoic membrane (CAM) model.
Figure 2B:
Figure 2C:
Figure 5A:
FIG. 5 illustrates the anti-angiogenic effect of SNS tripeptide analogues in the CAM model.
Figure 5B:
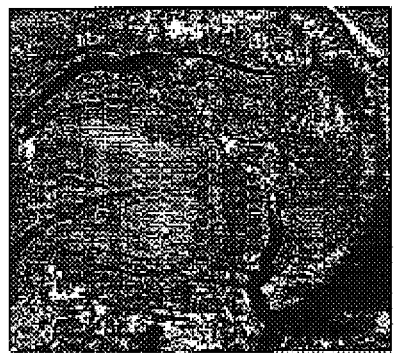
Figure 5C:
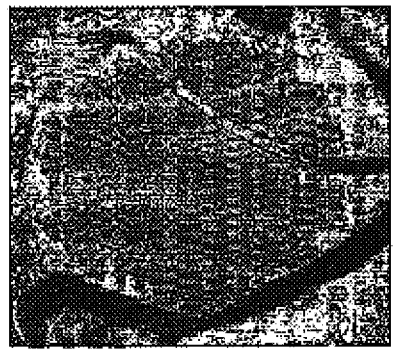
Figure 5D:
Figure 5E:
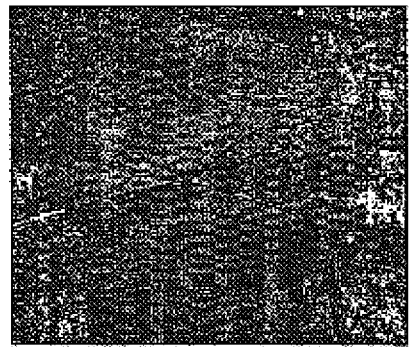
Figure 5F:
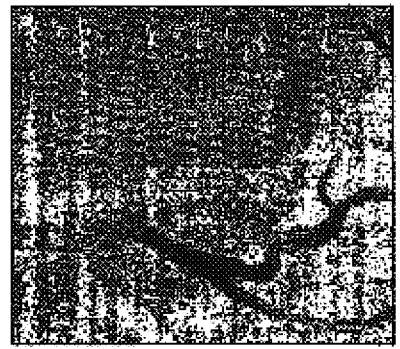
Figure 5G:
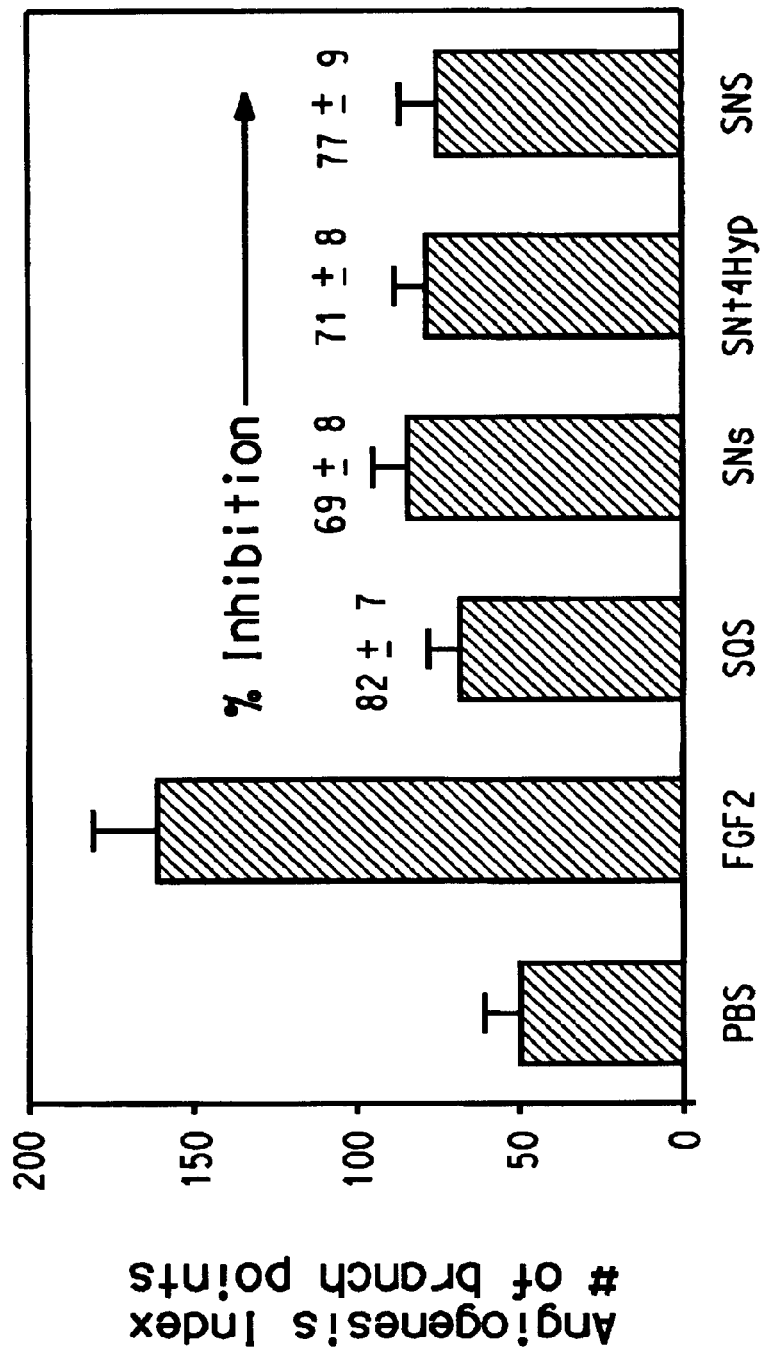

CAM tissue directly beneath FGF2-saturated filter disk was resected from embryos treated 48 h prior with compound or control. Tissues were washed three times with PBS. Sections were placed in a 35-mm petri dish (Nalge Nunc, Rochester, N.Y.) and examined under a SV6 stereomicroscope (Karl Zeiss, Thornwood, N.Y.) at 50× magnification. Digital images of CAM sections adjacent to filters were collected using a 3-CCD color video camera system (Toshiba America, New York, N.Y.) and analyzed with the Image-Pro Plus software (Media Cybernetics, Silver Spring, Md.) and can be seen in FIG. 2. Table 3 contains the number of vessel branch points contained in a circular region equal to the area of a filter disk counted for each section. Percent inhibition data is expressed as the quotient of the experimental value minus the negative control value divided by the difference between the positive control value and the negative control value.

TABLE 3

Average % Inhibition of Angiogenesis in the CAM Model

| Sample | Average # of Branch Points |
| --- | --- |
| PBS control | 94.714 |
| FGF2 control | 263.88 |
| Difference | 169.16 |
| FGF-2 + 16 µg acetyl-SNS-carboxamide | 91.60 |
| % Inhibition of branch point formation | 100.23 |

EXAMPLE 3

Chick Chorioallantoic Membrane Tumor Assays

Ten Million tumor cells were placed on the surface of each CAM and were cultured for one week. The resulting tumors were excised and cut into 50 mg fragments. These fragments were placed on additional CAMs and treated topically or systemically by intravenous injection the following day with the test agents. Forty-eight hours later, CAMs were excised from the egg and the number of blood vessels entering the tumors were counted (as vessel branch points). Data is presented as mean blood vessel number per treatment group (+/− standard error of measurement). Each treatment group incorporated at least ten tumors per experiment. Tumors were then excised from the egg and tumor weights were determined for each tumor. Data is presented in Table 3 as mean tumor weight per treatment group (+/− standard error of measurement). Statistical analyses were performed using Student's t-test. Results from this assay as depicted in Table 3, showed that 16 µg of acetyl-Ser-Asn-Ser-carboxamide (Structure 1) was effective in controlling FGF2-stimulated new blood vessel formation in the CAM (100%$_{ave}$ inhibition at 16 µg).

EXAMPLE 4

Inhibition of TSU-Pr (Prostrate) Tumor Growth

Ten million tumor cells were placed on the surface of each CAM (7-d old embryo) and were cultured for one week. The resulting tumors were excised and cut into 50 mg fragments. These fragments were placed on additional CAMs and treated topically the following day with acetyl-Ser-Asn-Ser-carboxamide (Structure 1) or vehicle. Seven days later, CAMs were excised from the egg and the number of blood vessels entering the tumors was counted (as vessel branch points). Data is presented as mean blood vessel number per treatment group (±standard error of measurement). Each treatment group incorporated at least ten tumors per experiment. Representative tumors were photographed at 10× magnification. Tumors were then excised from the egg and tumor weights were determined for each tumor. Data is presented as mean tumor weight per treatment group (±standard error of the mean). Statistical analysis was performed using Student's t-test.

Acetyl-Ser-Asn-Ser-carboxamide (Structure 1) was shown to inhibit the growth of human prostrate tumors in vivo by direct injection into the tumors (FIG. 3). Six tumors out of the ten injected with 45 µg acetyl-Ser-Asn-Ser-carboxamide (Structure 1) showed significant weight shrinkage after 7 d (111%$_{ave}$ inhibition at 45(100%$_{ave}$ inhibition at 16 µg).

EXAMPLE 5

Preparation of Library Based on Acetyl-Ser-Asn-Ser-Carboxamide

Based on the observed anti-angiogenic activity of acetyl-Ser-Asn-Ser-carboxamide (Structure 1) the following fifteen peptides were prepared using standard FMOC solid phase peptide chemistry (see General Methods): SAS, SQS, sNS, snS, SGS, SES, sNs, sns, SDS, SnS, SNs, Sns, t4Hyp-NS, t4Hyp-N-t4Hyp and SN-t4Hyp. The capital letters signify L-amino acids (natural), the small letters signify D-amino acids (unnatural) and t4Hyp signifies trans-4-hydroxyproline.

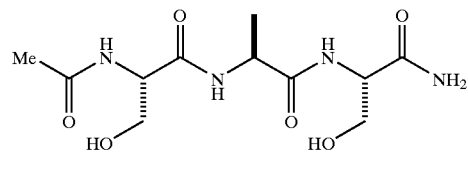

SAS C$_{11}$H$_{20}$N$_4$O$_6$
Exact Mass 304.14
Mol Wt 304.30
C, 43.42; H, 6.62; N, 18.41; O, 31.55

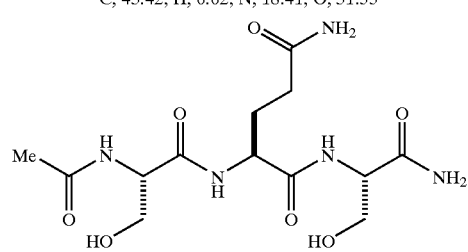

SQS C$_{13}$H$_{23}$N$_5$O$_7$
Exact Mass 381.16
Mol Wt . 381.35
C, 43.21; H, 6.42; N, 19.38; O, 30.99

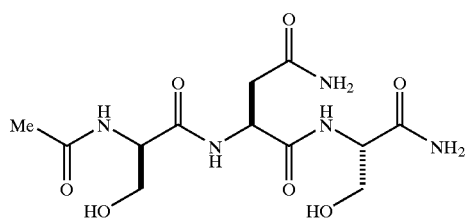

sNS C$_{12}$H$_{21}$N$_5$O$_7$
Exact Mass 347.14
Mol. Wt., 347.32
C, 41.50; H, 6.09; N, 20.16; O, 32.25

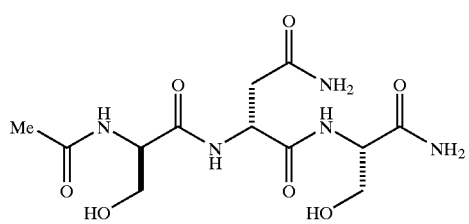

snS C$_{12}$H$_{21}$N$_5$O$_7$
Exact Mass 347.14
Mol Wt . 347.32
C, 41.50, H, 8 09; N, 20 16; O, 32.25

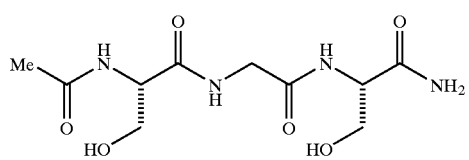

SGS C$_{10}$H$_{18}$N$_4$O$_6$
Exact Mass 290.12
Mol Wt . 290.27
C, 41.38; H, 6.25; N, 19.30; O, 33.07

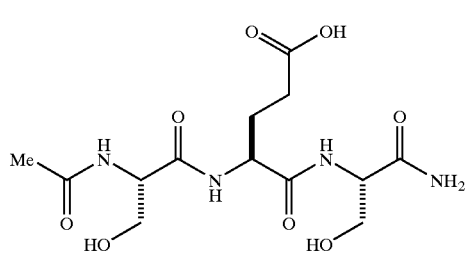

SES C$_{13}$H$_{22}$N$_4$O$_8$
Exact Mass 362.14
Mol Wt. 362.34
C, 43.09; H, 6.12; N, 15.46; O, 35.33

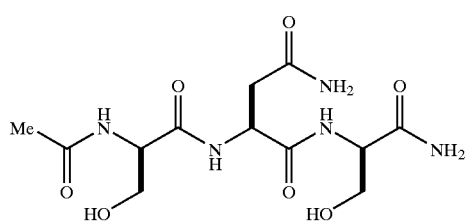

sNs C$_{12}$H$_{21}$N$_5$O$_7$
Exact Mass 347.14
Mol Wt. 347.32
C, 41.50; H, 6 09; N, 20.16; O, 32. 25

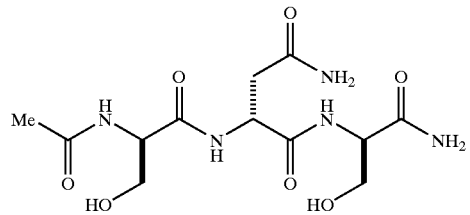

sns C$_{12}$H$_{21}$N$_5$O$_7$
Exact Mass 347.14
Mol Wt. 347.32
C, 41 50; H, 6.09; N, 20. 16; O, 32.25

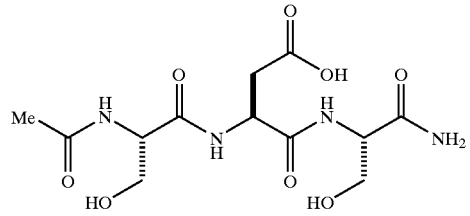

SDS C$_{12}$H$_{20}$N$_4$O$_8$
Exact Mass; 348.13
Mol Wt. 348.31
C, 41.38; H, 5.79; N, 16.09; O, 38.75

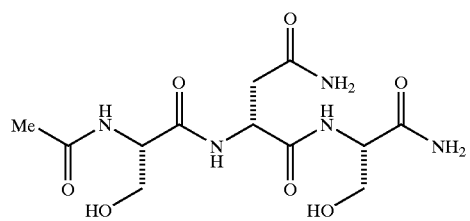

SnS C$_{12}$H$_{21}$N$_5$O$_7$
Exact Mass 347.14
Mol. Wt., 347.32
C, 41.50; H, 6.09; N, 20.16; O, 32.25

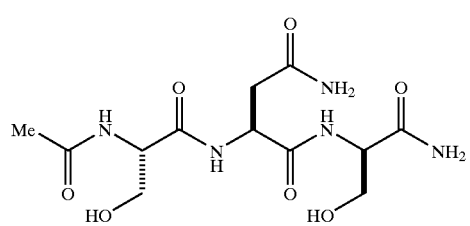

SNs C$_{12}$H$_{21}$N$_5$O$_7$
Exact Mass 347.14
Mol Wt. 347.32
C, 41.50; H, 8.09; N, 20.16; O, 32.25

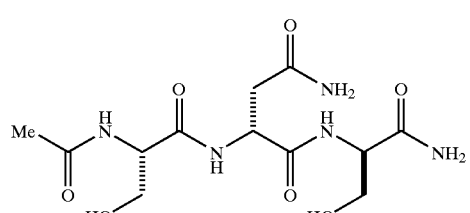

Sns C$_{12}$H$_{21}$N$_5$O$_7$
Exact Mass 347.14
Mol Wt. 347.32
C, 41.50; H, 6.09, N; 20.16; O, 32.25

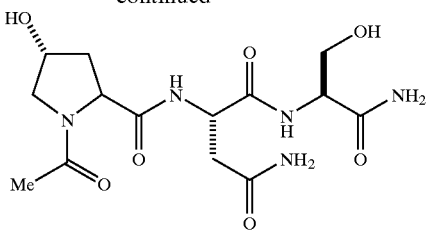

t4Hyp-NS C$_{14}$H$_{23}$N$_5$O$_7$
Exact Mass 373.18
Mol Wt. 373.36
C, 45.04, H; 6.21; N, 18.76; O, 30.00

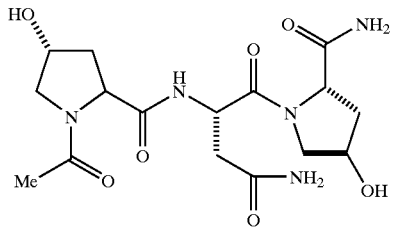

t4Hyp-N-t4Hyp C$_{18}$H$_{25}$N$_5$O$_7$
Exact Mass 399.18
Mol Wt. 399.40
C, 48.12; H, 6.31; N, 17.53; O, 28.04

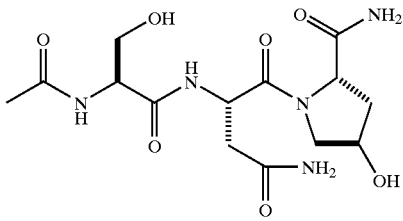

SN-t4Hyp C$_{14}$H$_{23}$N$_5$O$_7$
Exact Mass 373.18
Mol Wt. 373.36
C, 45.04; H, 6.21; N, 18.76; O, 30.00

The above fifteen peptides and acetyl-Ser-Asn-Ser-carboxamide (Structure 1) were tested for their anti-angiogenic effect in human endothelial tube formation as described in Example 1 (FIG. 4). The three most potent compounds SQS, SNs and SN-t4Hyp were also tested in the CAM assay as describe in Example 2 (also in FIG. 4). FIG. 5 illustrates the angiogenesis inhibiting effect of the SNS tripeptide analogues in the CAM model. Table 4 shows dose response data for SQS, SNs and SN-t4Hyp analogs in the CAM assay.

TABLE 4

% Inhibition of Branch Points in FGF2-Induced CAM Assay

| Concentration µg/CAM | SQS | SNs | SN-t4Hyp |
|---|---|---|---|
| 1 | 101% +/- 7 | 62% +/- 7 | 39% +/- 11 |
| 5 | 121% +/- 6 | 78% +/- 6 | 60% +/- 7 |
| 15 | 82% +/- 7 | 69% +/- 8 | 71% +/- 8 |

What is claimed is:

1. An angiogenesis-inhibitory tripeptide of formula aa1-aa2-aa3, having a first amino acid (aa1), a second amino acid (aa2) and a third amino acid (aa3), wherein:
    (a) said first amino acid is selected from the group consisting of Ser, Thr, Ala, Phe, Tyr, Cys, Gly, Leu, Lys, Pro, Arg, Gln, Glu, Asp, Asn, His, Met, Ile, Trp, Val, diaminoproprionic acid and trans-4-hydroxy-proline;
    (b) said second amino acid is selected from the group consisting of Asn, Ala, Gly, Asp, Glu, Gln diaminoproprionic acid and trans-4-hydroxy-proline; and
    (c) said third amino acid is selected from the group consisting of Ser, Thr, Ala, Phe, Tyr, Cys, Gly, Leu, Lys, Pro, Arg, Gln, Glu, Asp, Asn, His, Met, Ile, Trp, Val, diaminoproprionic acid and trans-4-hydroxy-proline;

and wherein the tripeptide is not Arg-Gly-Asp, Asn-Gly-Arg, or Gly-Ser-Leu.

2. The angiogenesis-inhibitory tripeptide of claim 1, wherein:
    (a) said first amino acid is selected from the group consisting of Ser, Thr, Cys, and diaminoproprionic acid;
    (b) said second amino acid is selected from the group consisting of Asn and Gln; and
    (c) said third amino acid is selected from the group consisting of Ser, Thr, Cys, trans-4-hydroxy-proline, and diaminoproprionic acid.

3. The angiogenesis-inhibitory tripeptide of claim 1, wherein:
    (a) said first amino acid is Ser;
    (b) said second amino acid is Asn or Gln; and
    (c) said third amino acid is Ser or trans-4-hydroxy-proline.

4. The angiogenesis-inhibitory tripeptide of claim 1, wherein the tripeptide is capped, wherein said tripeptide is not capped with an amino acid or peptide.

5. The angiogenesis-inhibitory tripeptide of claim 1, wherein the first amino acid is an amino-terminal and the third amino acid is a carboxy-terminal, wherein:
    (a) the amino-terminal is capped with a compound selected from the group consisting of acetyl, benzoyl, alkylsulfonyl, arylsulfonyl, alkylaminoacyl, arylaminoacyl, and formyl; and
    (b) the carboxy-terminal is capped with a compound selected from the group consisting of NH$_2$, OH, and NHR, wherein R is selected from the group consisting of alkyl and aryl.

6. The angiogenesis-inhibitory tripeptide of claims wherein the amino-terminal is capped with an acetyl group and the carboxy-terminal is capped with an NH$_2$ group.

7. An angiogenesis-inhibitory composition, comprising the angiogenesis-inhibitory tripeptide of claim 1.

8. A pharmaceutical composition useful as an angiogenesis inhibitor, the composition comprising an angiogenesis-inhibitory amount of the angiogenesis-inhibitory tripeptide of claim 1.

9. A method of inhibiting angiogenesis in a tissue, the method comprising administering to the tissue an angiogenesis-inhibitory amount of the tripeptide of claim 1.

10. A method of inhibiting angiogenesis in an animal, the method comprising administering to the animal an angiogenesis-inhibitory amount of the tripeptide of claim 1.

11. A method of inhibiting angiogenesis in an individual, the method comprising administering to the individual an angiogenesis-inhibitory amount of the tripeptide of claim 1.

12. The method of claim 9, wherein the tissue is inflamed.

13. The method of claim 9, wherein said tissue is selected from the group consisting of solid tumor, solid tumor metastases, retinal tissue, and choroidal tissue.

14. The method of claim 9, wherein the angiogenesis is associated with a condition selected from the group consisting of ocular neovascular diseases, choroidal neovascular diseases, retina neovascular diseases, neovascularization of the angle, Bartonellosis, chronic inflammation, osteoarthritis, rheumatoid arthritis, atherosclerosis phemphigoid, trachoma, and Osler-Webber-Rendu disease.

15. The method of claim 9, wherein said tripeptide is administered via a pharmaceutically acceptable medium.

16. The method of claim 9, wherein said tripeptide is administered via osmoticmini-pumps.

17. The method of claim 9, wherein said tripeptide is administered via biodegradable polymers.

18. The method of claim 9, wherein said tripeptide is administered by encoding a nucleic acid for the angiogenesis-inhibitory tripeptide of claim 1.

19. The method of claim 9, wherein said administering is carried out by incorporation into a vector, said vector being selected from the group consisting of retrovirus, adenovirus, ligand conjugated nucleic acids, isolated DNA, isolated RNA, liposomes, and polylysines.

20. The method of claim 11, wherein said administering is selected from the group consisting of oral, topical, nasal, transdermal, intraperitoneal, intracranial, intracerebral, vaginal, intrauterine, rectal, parenteral, and ophthalmic administration.

21. The method of claim 11, wherein said tripeptide is administered in conjunction with a therapeutic compound, the therapeutic compound being selected from the group consisting of chemotherapeutics, antibiotics, antivirals, anti-inflammatories, targeting compounds, cytokines, immunotoxins, anti-tumor antibodies, angiogenic inhibitors, anti-edema agents, and radiosensitizers.

22. The method of claim 11, wherein said tripeptide is administered in conjunction with a therapeutic method, the therapeutic method being selected from the group consisting of surgery, chemotherapy, radiation and laser therapy.

23. An angiogenesis-inhibitory compound, comprising capped tripeptide of formula aa1-aa2-aa3, having a first amino acid (aa1), a second amino acid (aa2) and a third amino acid (aa3), wherein:

(a) said first amino acid is selected from the group consisting of Ser, Thr, Ala, Phe, Tyr, Cys, Gly, Leu, Lys, Pro, Arg, Gln, Glu, Asp, Asn, His, Met, Ile, Trp, Val, diaminoproprionic acid and trans-4-hydroxy-proline and wherein said first amino acid is capped with a polymer;

(b) said second amino acid is selected from the group consisting of Asn, Ala, Gly, Asp, Glu, Gln diaminoproprionic acid and trans-4-hydroxy-proline; and (c) said third amino acid is selected from the group consisting of Ser, Thr, Ala, Phe, Tyr, Cys, Gly, Leu, Lys, Pro, Arg, Gln, Glu, Asp, Asn, His, Met, Ile, Trp, Val, diaminoproprionic acid and trans-4- hydroxy-proline and wherein said third amino acid is capped with a compound selected from the group consisting of $NH_2$, OH, and NHR, wherein R is selected from the group consisting of alkyl and aryl;

and herein the tripeptide is not Arg-Gly-Asp, Asn-Gly-Arg, or Gly-Ser-Leu.

* * * * *